United States Patent [19]

D'Auria

[11] 4,019,516
[45] Apr. 26, 1977

[54] EYE SHIELD DEVICE
[75] Inventor: Rosemarie D'Auria, Jersey City, N.J.
[73] Assignee: The Raymond Lee Organization, Inc., New York, N.Y.; a part interest
[22] Filed: Nov. 10, 1975
[21] Appl. No.: 630,677
[52] U.S. Cl. .............................. 128/268; 128/260
[51] Int. Cl.² ........................................ A61F 7/02
[58] Field of Search ............... 128/260, 268; 2/12; 351/49

[56] References Cited
UNITED STATES PATENTS

| | | | |
|---|---|---|---|
| 2,342,840 | 2/1944 | Cadous | 128/268 |
| 2,343,157 | 2/1944 | Quering | 128/268 X |
| 3,333,586 | 8/1967 | Bellis et al. | 128/268 |

Primary Examiner—Aldrich F. Medbery
Attorney, Agent, or Firm—Daniel Jay Tick

[57] ABSTRACT

An eye covering member of opaque material has an inner surface adjacent the eyes of a wearer when in use. A fastening device on the eye covering member removably affixes said member over the eyes of a wearer. A pair of eye pads are removably accommodated in a pair of spaced recesses formed in the inner surface of the eye covering member over the eyes of a wearer for applying medication to the eyes.

1 Claim, 5 Drawing Figures

EYE SHIELD DEVICE

DESCRIPTION OF THE INVENTION

The present invention relates to an eye shield device.

Objects of the invention are to provide an eye shield device of simple structure, which is inexpensive in manufacture, used with facility and convenience by anyone, and functions efficiently, effectively and reliably to apply medication to the eyes of a wearer.

In order that the invention may be readily carried into effect, it will now be described with reference to the accompanying drawing, wherein.

Figure 1:
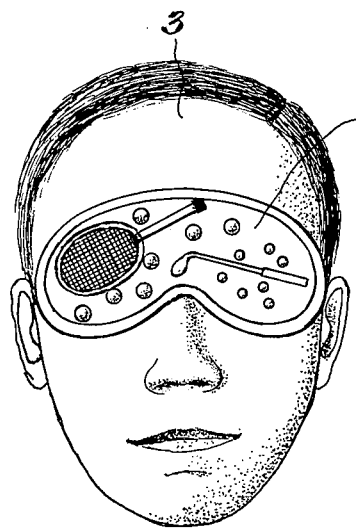
FIG. 1 is a view of an embodiment of the eye shield device of the invention in use by a wearer.
Figure 3:
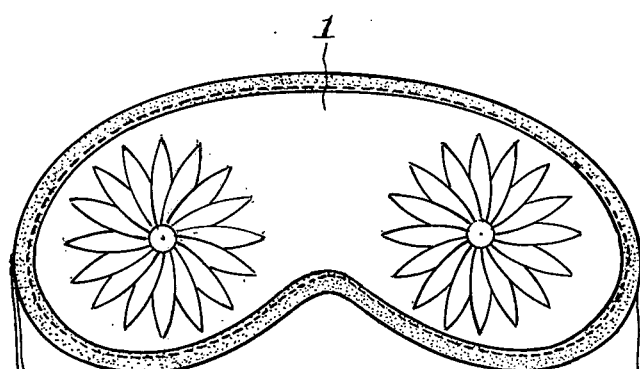
FIG. 3 is a view, on an enlarged scale, of the outside of an embodiment similar to FIG. 1 but having a different design.
Figure 4:
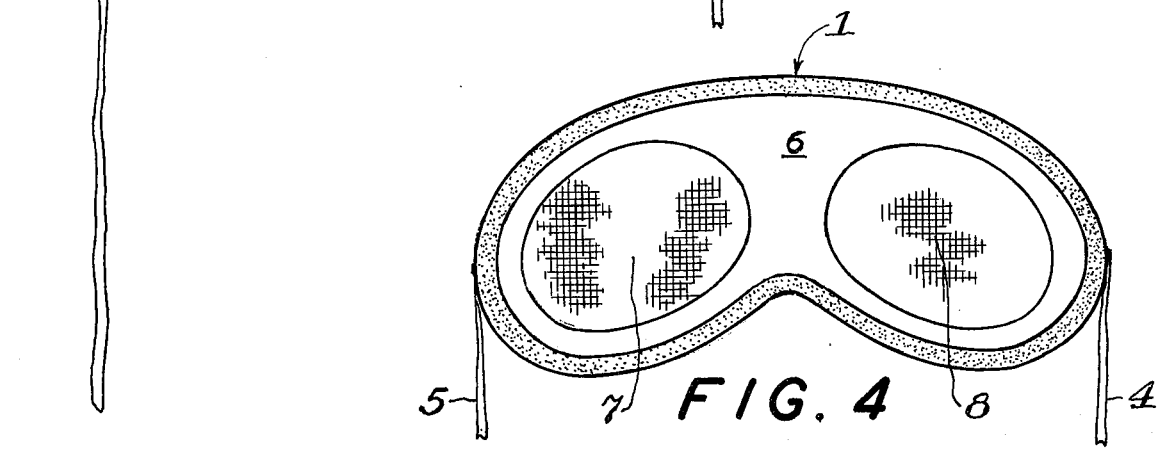
FIG. 4 is a view, on an enlarged scale, of the inside of the embodiment of FIG. 1.

The eye shield device of the invention comprises an eye covering member 1 (FIGS. 1, 3 and 4) of opaque material of any suitable type such as, for example, plastic, having an inner surface 2 adjacent the eyes of a wearer 3 (FIG. 1) when in use.

A fastening device of any suitable type such as, for example, two strips of ribbon 4 and 5 (FIGS. 3 and 4), is provided on the eye covering member 1 for removably affixing said member over the eyes of the wearer 3.

Figure 2:
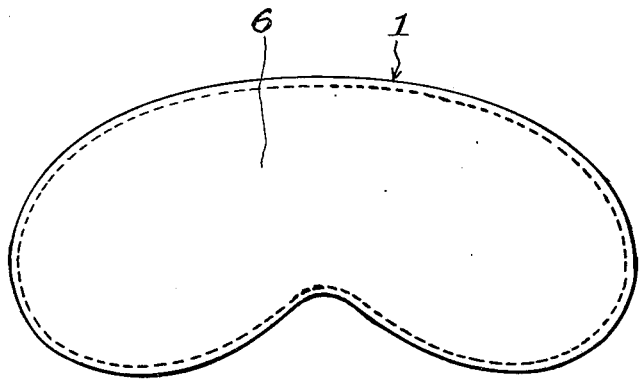
FIG. 2 is a view, on an enlarged scale, of internal padding of the embodiment of FIG. 1.

Various layers of padding material 6 are provided on the inner surface of the eye covering member 1, as shown in FIG. 2, and have a pair of spaced recesses 7 and 8 (FIG. 4) formed therein, the inner surface 2 of the eye covering member serving as a bottom or boundary for the recesses. The recesses 7 and 8 are formed over the eyes of the wearer 3.

Figure 5:
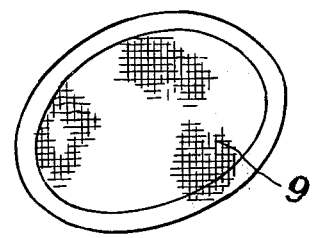
FIG. 5 is a view, on an enlarged scale, of an eye pad of the eye shield device of the invention.

A pair of eye pads, of which, a single eye pad 9 is shown in FIG. 5, are removably accommodated in the recesses 7 and 8. The eye pads may be saturated or soaked in medication or may have medication therein for application to the eyes of the wearer.

While the invention has been described by means of a specific example and in a specific embodiment, I do not wish to be limited thereto, for obvious modifications will occur to those skilled in the art without departing from the spirit and scope of the invention.

I claim:

1. An eye shield device, comprising an eye covering member comprising a unitary strip of opaque material having an inner surface adjacent the eyes of a wearer when in use;

layers of padding material affixed to the inner surface of the opaque material;

fastening means on the eye covering member for removably affixing said member over the eyes of a wearer;

a pair of spaced recesses formed in the layers of padding material and bounded by the adjacent inner surface of said unitary strip of the eye covering member over the eyes of a wearer; and a pair of medicated eye pads removably accommodated in said recesses for applying medication to the eyes of a wearer.

* * * * *